United States Patent [19]

Miller

[11] Patent Number: 4,670,379

[45] Date of Patent: Jun. 2, 1987

[54] POLYNUCLEOTIDE HYDRIDIZATION ASSAYS EMPLOYING CATALYZED LUMINESCENCE

[75] Inventor: Jeffrey A. Miller, Framingham, Mass.

[73] Assignee: E. I. Du Pont de Nemours and Company, Wilmington, Del.

[21] Appl. No.: 683,947

[22] Filed: Dec. 19, 1984

[51] Int. Cl.[4] ............................................. C12Q 1/68
[52] U.S. Cl. ......................................... 435/6; 435/28; 435/810; 436/501; 536/27; 536/28; 935/78
[58] Field of Search .................. 435/6, 8, 25, 28, 810; 436/501, 164, 172, 805, 808; 935/78; 536/27, 28

[56] References Cited

U.S. PATENT DOCUMENTS

| | | | |
|---|---|---|---|
| 4,238,565 | 12/1980 | Hornby et al. | 435/7 |
| 4,358,535 | 11/1982 | Falkow et al. | 435/5 |
| 4,366,243 | 12/1982 | Rupchock et al. | 435/7 |

FOREIGN PATENT DOCUMENTS

| | | |
|---|---|---|
| 0063879 | 11/1982 | European Pat. Off. . |
| 0070687 | 1/1983 | European Pat. Off. . |
| 0070685 | 1/1983 | European Pat. Off. . |
| 0079139 | 5/1983 | European Pat. Off. . |
| 0097373 | 1/1984 | European Pat. Off. . |
| 0110682 | 6/1984 | European Pat. Off. . |
| 0117440 | 9/1984 | European Pat. Off. . |
| 0122614 | 10/1984 | European Pat. Off. . |
| 0124221 | 11/1984 | European Pat. Off. . |
| 0128018 | 12/1984 | European Pat. Off. . |
| 0127327 | 12/1984 | European Pat. Off. . |
| 0128042 | 12/1984 | European Pat. Off. . |
| 83/02286 | 7/1983 | PCT Int'l Appl. . |
| 83/02277 | 7/1983 | PCT Int'l Appl. . |
| 84/01174 | 3/1984 | PCT Int'l Appl. . |
| 84/02721 | 7/1984 | PCT Int'l Appl. . |
| 2019408 | 10/1979 | United Kingdom . |
| 2125964 | 3/1984 | United Kingdom . |

OTHER PUBLICATIONS

Brandt and Keston, Analytical Biochemistry, 11:6, (1965).
Keston and Brandt, Analytical Biochemistry, 11:1, (1965).
Cathcart et al., Analytical Biochemistry 134:111, (1983).
Guilbault et al., Analytical Chemistry, 40, No. 8, p. 1256, (1968).
Klausen, et al., Biotechnology, p. 471, (1983).

*Primary Examiner*—Sidney Marantz

[57] ABSTRACT

Polynucleotide hydridization assays employing catalyzed luminescence.

16 Claims, No Drawings

POLYNUCLEOTIDE HYBRIDIZATION ASSAYS EMPLOYING CATALYZED LUMINESCENCE

FIELD OF THE INVENTION

This invention relates to polynucleotide hybridization assays wherein a catalyst-labeled first polynucleotide probe and an apoluminescer-labeled second polynucleotide probe are both hybridized with a complementary target polynucleotide analyte in a physiological sample. A substrate is added to the sample and is converted by the catalyst to a transformation radical which in turn converts the apoluminescer to a luminescer. The sample is irradiated, and the incident light absorbed by the luminescer is reemitted at a different wavelength. Such secondary emissions can occur only if hybridization has taken place and hence, the presence of the target polynucleotide is related to the amount of secondary light emitted.

BACKGROUND OF THE INVENTION

Polynucleotide hybridization assays are used as research tools for the detection and identification of unique or specific polynucleotide sequences in samples of complete, fragmented, or mixed nucleic acid. Various hybridization diagnostic techniques have been developed.

Southern, *J. Mol. Biol.*, 98:503 (1975), discloses a polynucleotide hybridization technique employing radiolabeled nucleic acid probes. This procedure permits autoradiographic detection of probe/analyte hybrids and identification of the polynucleotide sequence of the analyte. However, the Southern procedure, as well as the other diagnostic procedures employing radiolabeled nucleic acid probes, are very complex, time consuming, and have the additional problems and expenses generally associated with radioactive materials such as personnel monitoring and disposal. Thus, such assays have remained a tool of basic research and are not generally employed in applied or commercial areas such as clinical diagnosis.

Ward et al., European Patent Application No. 82301804.9, Publication No. 0063879, published June 4, 1982, discloses compositions useful as probes in biomedical research and recombinant DNA technology, wherein said probes comprise purine, 7-deazapurine or pyrimidine covalently coupled to a moiety capable of forming a detectable complex with a polypeptide, said moiety being coupled to purine bases at the 8-position, to deazapurine bases at the 7-position, or to pyrimidine bases at the 5-position to form a modified nucleotide. The resulting modified nucleotides are incorporated into DNA by nick-translation techniques.

Ranki, European Patent Application No. 82306489.5, Publication No. 0079139, published May 18, 1983, discloses a technique for the sandwich hybridization of nucleic acids, said technique comprising contacting single-stranded nucleic acid from a microorganism with a pair of different nucleic acid reagents, both reagents of the pair being single-stranded and complementary with the microorganism-derived nucleic acid and one of the pair being a nucleic acid fragment attached to a solid carrier, such as a nitrocellulose filter, while the other is a nucleic acid fragment labeled with a radioactive marker, whereby a labeled hybrid is formed attached to the solid carrier, for the identification of a microorganism or group of microorganisms present in a sample. The correctness of the identification is tested by detection of the extent of formation of a labeled hybrid attached to the solid carrier.

Tchen et al., PCT Application No. PCT/FR82/00220, published July 7, 1983, disclose nucleic acid probe compositions which have been chemically modified by the covalent attachment of at least one N-2-acetylaminofluorene group to one of the bases of the nucleic acid. After hybridization with the target homologous nucleic acid sequence, such hybridization may be detected by the use of enzyme-labeled antibodies.

Kourilsky et al., PCT Application No. PCT/FR82/00223 published July 7, 1983, disclose DNA molecules modified by covalent attachment of an oligomer of modified ribonucleotides, or a single modified ribonucleotide, which provides a means for coupling a chemical capable of recognition by another molecule or product.

Co-pending and commonly assigned U.S. application Ser. No. 574,630, discloses polynucleotide probe compositions which contain a polypeptide moiety capable of enzymatically activating a zymogen to initiate a detectable enzymatic reaction cascade.

Falkow et al., U.S Pat. No. 4,358,535 issued Nov. 9, 1982, disclose a method for detecting the presence of a pathogen in a clinical sample by depositing and fixing said sample on an inert support and hybridizing the genetic material of the target pathogen to a labeled-nucleic acid probe. The label may be a radioisotope, a ligand, a fluorescer, a chemiluminescer, an enzyme, or an antibody.

Kourilsky et.al., U.K. patent application No. 7913031, Publication No. 2019408A published Oct., 31, 1979, disclose a method for detecting the possible presence of a DNA fragment in a sample comprising the hybridization of the sought fragment with an RNA probe which is coupled to an enzyme either prior to or subsequent to the hybridization reaction. The possible presence of the target nucleic acid sequence is revealable by the action of the enzyme-labeled hybridization product on a chromogen substrate.

Heller et al., European patent application No. 82303701.5, Publication No. 0070687, published Jan. 26, 1983, disclose a heterogeneous hybridization diagnostic method which uses luminescer-labeled, single-stranded polynucleotide reagents for hybridizing with immobilized sample single-stranded polynucleotides. After separation of the unhybridized reagent, the sample is exposed to light. Any subsequent light emission is related to the amount of target polynucleotide in the sample. The label may be any of the well known luminescent systems.

Heller et al., European patent application No. 82303699.1, Publication No. 0070685, published July 14, 1982, disclose a homogeneous light-emitting hybridization assay wherein luminescer-labeled first and second single-stranded reagent segments are hybridized with a complementary target single-stranded polynucleotide from a physiological sample such that nonradioactive energy transfer occurs between the labels of the two reagent segments. At least one of the labels is of the absorber/emitter type such that energy in the form of a photon absorbed from the other light label is re-emitted as a different wavelength. Such secondary emissions can only occur if hybridization has taken place. This system, however, suffers the disadvantage of requiring two luminescer-labeled probes of absorber/emitter character distinct enough to be able to differentiate one from the other by photometric means. Such differentiation may be difficult in complex physiological samples.

The enzyme catalyzed conversion of apoluminescer to luminescer is known. Brandt et al., *Anal. Biochem.*, II, 6 to 9 (1965); and Keston et al. *Anal. Biochem.*, II, 1 to 5 (1965); disclose the conversion of the nonfluorescent apofluorophore diacetyl 2',7'-dichlorofluorescen to a fluorescent compound by hydrogen peroxide and peroxidase for the fluorometric analysis of ultramicro quantities of hydrogen peroxide. Guilbault et al. *Anal. Chem.*, 40 (8), 1256 to 1263 (1968); Brunvoll, *Acta Chem. Scand.*, 21 (3), 820 to 821 (1967): and Guilbault et al., *Anal. Chem.*, 39 (2), 271 (1967), disclose the conversion of the nonfluorescent apofluorophores homovanillic acid, p-hydoxyphenylacetic acid, tyrosine or tyramine to a fluorescent compound by hydrogen peroxide and peroxidase for the fluorometric analysis of ultramicro quantities of hydrogen peroxide. Cathcart, *Anal. Biochem.*, 134, 111 to 116 (1983), discloses the conversion of nonfluorescent apofluorophores to fluorescent compounds by hydrogen peroxide and hematin for the fluorometric detection of picomole levels of hydrogen peroxide. The Cathcart reference also discloses that alternate peroxides could be employed in place of hydrogen peroxide as the substrate for peroxidase or hematin. None of the above references disclose or suggest the use of apofluorophores as labels for polynucleotide probes.

There is a need in the area of clinical diagnostics for a nonradiometric homogeneous assay which is fast simple to carry out, highly specific and highly sensitive. The assay of the present invention fulfills this need.

SUMMARY OF THE INVENTION

The subject invention relates to polynucleotide probe compositions of the formulas $$(X_1-X_n) \text{ and } (Y_1-Y_n)$$

wherein n is an integer from 2 to about 500;

$X_1$ through $X_n$, which are the same or different, are nucleotide moieties which collectively form a polynucleotide sequence substantially complementary to a single-stranded region of a target polynucleotide analyte A; provided that at least one of nucleotide moieties $X_1$ through $X_n$ comprises a moiety Z where Z comprises a nucleotide having a catalyst attached thereto capable of generation, from a substrate, of a transformation radical which, in turn, is capable of transforming an apoluminescer into a luminescer; and $Y_1$ through $Y_n$, which are the same or different, are nucleotide moieties which collectively form a polynucleotide sequence substantially complementary to a single-stranded region of polynucleotide analyte A different from, but proximate to, the region to which $X_1$ through $X_n$ is complementary; provided that at least one of nucleotide moieties $Y_1$ through $Y_n$ comprises a moiety Z' where Z' comprises a nucleotide having an apoluminescer attached thereto capable of being transformed into a luminescer by the transformation radical generated by the activity of the catalyst of $(X_1-X_n)$; further provided that $(X_1-X_n)$ and $(Y_1-Y_n)$ are selected such that upon hybridization with A, the catalyst of $(X_1-X_n)$ is sufficiently proximate the apoluminescer of $(Y_1-Y_n)$ to effect the desired transformation of apoluminescer to luminescer upon introduction of the appropriate substrate.

The subject invention also relates to a method for detecting the presence of a target polynucleotide analyte in a physiological sample, wherein the method comprises:

(a) contacting the sample, under hybridization conditions, with a first and a second polynucleotide probe, the first probe having a catalyst attached thereto and the second probe having an apoluminescer attached thereto, both probes being substantially complementary to substantially mutually exclusive single-stranded regions of the analyte, such that upon hybridization of both probes with the analyte, the catalyst and the apoluminescer are located close enough to each other to permit the catalyst to react with a substrate a transformation radical that subsequently transforms the apoluminescer to a luminescer;

(b) adding the substrate for the catalyst the substrate being capable of conversion to a transformation radical by the catalyst, the radical being capable of converting the apoluminescer to a luminescer;

(c) irradiating the sample with incident light within the absorption spectrum of the luminescer; and (d) measuring the light emitted by the luminescer.

The subject invention also relates to a diagnostic kit for detecting the presence of a target polynucleotide analyte in a physiological sample, wherein the kit comprises:

(a) a first polynucleotide probe having a catalyst attached thereto and which is substantially complementary to a first single-stranded region of the analyte;

(b) a second polynucleotide probe having an apoluminescer attached thereto and which is substantially complementary to a second single-stranded region of the analyte; the second region being substantially mutually exclusive from the first region, such that upon hybridization of the first and second probes with the analyte, the catalyst and the apoluminescer are close enough to each other to permit the catalyst to act on a substrate to release a transformation radical to convert the apoluminescer to a luminescer; and preferably (c) a substrate for the catalyst, the substrate being capable of conversion to a transformation radical by the catalyst, the radical being capable of converting the apoluminescer to a luminescer.

DETAILED DESCRIPTION OF THE INVENTION

The present invention provides polynucleotide probe compositions, diagnostic kits, and nonradiometric hybridization assays useful in the detection and identification of at least one target polynucleotide analyte in a physiological sample. The sensitivity and specificity of the probes, kits, and assays of the present invention render them widely useful in clinical diagnosis and biological research. Examples of uses for the probes, kits and assays of the present invention include characterization of genetic disorders, detection of particular viruses, microbes or other organisms, and identification of specific nucleotide base sequences.

As used herein, the term "target polynucleotide analyte" refers to a segment of single-stranded polynucleotide having a nucleotide base sequence corresponding to a genetic element whose presence in a physiological sample is to be detected and/or identified.

As used herein, the term "substantially complementary" refers to sufficient nucleotide base sequence homology between a polynucleotide probe and its target analyte to permit formation of stable probe-analyte hybrids.

As used herein, the term "physiological sample" means a sample of blood, urine or other biological tissue, either unprocessed or processed, containing the DNA or RNA of interest.

As used herein, the term "substantially mutually exclusive" means that upon hybridization by the first and second probes with each target analyte, the two probes should not compete for the same nucleotide base sequence on the analyte to the extent that hybridization is prevented. In one particular embodiment, spacing of the two DNA probes would have the 3'-terminal nucleotide of the first probe approximately ten bases away from the 5'-terminal nucleotide of the second probe. This will space the termini such that they are on the same side of the helix and thus position the catalyst and apoluminscer groups in the most favorable position with respect to each other.

As used herein, the term "hybridization conditions" means those conditions which will enable the first and second probes to form stable probe-analyte hybrids. The proper hybridization conditions will be determined by the nature of the catalyst and apoluminescer employed, the length of the nucleotide polymer of the labeled probes, and the guanosine plus cytosine content of the probes and/or the target polynucleotide analyte.

The term "fluorescent" generally refers to luminescent compounds having the characteristic of re-emitting absorbed incident energy in about $10^{-8}$ to $10^{-3}$ seconds, while the term "phosphorescent" refers to luminescent compounds which take longer to re-emit absorbed incident energy. Also, depending upon the source of incident energy (i.e. photons, charged particles, chemical phenomena etc.) luminescent compounds are referred to as chemiluminescent, bioluminescent, electroluminescent, photoluminescent, etc.

The term "apoluminescer" refers to any nonluminescent compound which, upon activation by a "transformation radical", converts to a luminescer. Likewise, the term "catalyst" (e.g., an enzyme) as used herein refers to compositions which are capable of releasing an appropriate transformation radical from a substrate for that catalyst.

For example, a hydroxy ($OH^-$) transformation radical can be produced by any of the well known catalysts (e.g., horseradish peroxidase, hematin, metal cation, especially EDTA-Fe III complexes, microperoxidase, and other redox enzymes) acting upon an appropriate substrate (e.g., molecular oxygen, hydrogen peroxide, HCOOH, $H_3$CCOOH, t-butylhydroperoxide, linoleic hydroperoxide, cholesterol 5-hydroperoxide and cumen hydroperoxide). The ($OH^-$) radical will then convert the apoluminescer to the corresponding luminecescer (e.g. activated diacetyldichlorofluorescin to dichloroflourescein, homovanillic acid to 2,2'-dihydroxy-3,3'-dimethoxybiphenyl-5,5'-diacetic acid, p-hydroxyphenylacetic acid to 2,2'-dihydroxybiphenyl-5,5'-diacetic acid, tyrosine to 2,2'-dihydroxybiphenyl-5,5'-dialanine, tyramine to 2,2'-dihydroxybiphenyl-5,5'-diethylamine, luminol to 3-aminophthalic acid plus light, and p-hydroxyphenylpropionic acid to 2,2'-dihydroxybiphenyl-5,5'-dipropionic acid).

These catalysts, substrates and apoluminescers are readily available from many commercial sources.

As used herein, "polynucleotide" refers to a polymer of ribonucleic acid (RNA) or deoxyribonucleic acid (DNA), which can be single- or double-stranded, optionally incorporating or comprising synthetic, non-natural, or altered nucleotides capable of incorporation into DNA or RNA polymers. Probe polynucleotides, ($X_1$—$X_n$) and ($Y_1$—$Y_n$) can be conveniently isolated in useful quantities by cloning and amplification of polynucleotide sequences complementary to target polynucleotides in plasmid or phage vectors, using techniques that are now conventional to those skilled in the art. A useful reference covering most aspects of DNA manipulation is Maniatis et al., *Molecular Cloning, A Laboratory Manual.* (Cold Spring Harbor Laboratory, 1982), the disclosure of which is incorporated herein by reference.

An exemplary cloning vehicle for production of useful quantities of probe polynucleotides is plasmid pBR322 (ATCC 37017), which is described in detail by Rodriquez, et al., in Scott, ed., *Molecular Cloning of Recombinant DNA*, (Academic Press, New York, 1977), p. 73. This plasmid contains single PstI. BamI, EcoRI, HindIII, and SalI restriction endonuclease recognition sites, in addition to genes conferring resistance to the antibiotics tetracycline and ampicillin. plasmid DNA can be amplified by growth in the presence of chloramphenicol (170 μg/ml) according to the method of Clewell, *J. Bacteriol.* 110:667 (1972); and purified by the cleared lysate procedure of Guerry et al., *J. Bacteriol.* 116:1064 (1973), prior to digestion with an appropriate endonuclease. For example, digestion with pstI inactivates the ampicillin resistance marker and generates "sticky ends" suitable for ligation to a probe polynucleotide similarly cleaved with PstI. The resulting recombinant plasmid can then be employed to transform a suitable host bacterium, e.g., E. coli K12 HB1O1. Upon growth in the presence of chloramphenicol, high plasmid copy numbers can be attained and the recombinant plasmid DNA isolated and purified as previously described.

However, a particularly preferred vector for production of probe polynucleotides is a coliphage, M13, (ATCC 15669-Bl) which, like pBR322, is now commercially available (New England Nuclear Corporation, Boston, Mass., USA). DNA fragments obtained by digestion of phage DNA and DNA complementary to a target DNA of interest can be joined, amplified, and subsequently purified in single-stranded form prior to conjugation with a reporter molecule, e.g., an enzymatic activator polypeptide such as peroxidase. The use of M13 phage as a cloning vehicle has been described by Messing, *Recombinant DNA Tech. Bull.* 2:43, (1979), the disclosure of which is hereby incorporated by reference.

Z and Z' of the present invention are nucleotide moieties within ($X_1$—$X_n$) and ($Y_1$—$Y_n$) respectively. Of course, the catalyst and apoluminescer of Z and Z' need be close enough together (after hybridization of ($X_1$—$X_n$) and ($X_1$—$Y_n$) with the target analyte) so that the transformation radical resulting from the activity of the catalyst can transform the apoluminescer to a luminescer. In this regard, the placement of Z and Z' on probes ($X_1$—$X_n$) and ($Y_1$—$Y_n$) should result, after hybridization, in Z and Z' being no more than about 100 base-pairs apart. Preferably, Z and Z' are located at the 3' terminal position of ($X_1$—$X_n$) and the 5' terminal position of ($Y_1$—$Y_n$) respectively (or vice versa) so that upon hybridization of both probes with the target analyte, the labeled 3' terminal position of one of the probes will become continuous (lined up head to tail) with the labeled 5' terminal position of the other probe. Thus, if the catalyst-labeled probe is labeled at its 3' terminal position, the apolumlnesoer-labeled probe should be labeled at its 5' terminal position so that, after hybridization, the catalyst is within none or a few analyte nucleotide base pairing spaces of the apoluminescer.

Z and Z' can be independent nucleotide units which are inserted by known techniques (e.g., nick-translation or direct synthetic routes) into $(X_1—X_n)$ and $(Y_1—Y_n)$ respectively, or nucleotides within $(X_1—X_n)$ and/or $(Y_1—Y_n)$ may be modified to produce Z and Z'. In either case, Z and Z' are nucleotide moieties of the formula

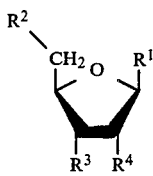

wherein
$R^1$ is $BR^5$;
where
B is a base residue; and
$R^5$ is H or T, where T is a catalyst in the case of Z, and an apoluminescer in the case of Z';
$R^2$ and $R^3$ are H, OH, T, a phosphate group or groups, an adjacent nucleotide moiety, a phosphate group covalently linked to a moiety T or to an adjacent nucleotide moiety or a phosphate group covalently linked to a moiety T and an adjacent nucleotide moiety; and
$R^4$ is H, OH, a phosphate group, or T; provided that, for at least one of nucleotide moieties $X_1$ through $X_n$, $R^1$ is $BR^5$ and $R^5$ is T (a catalyst), and for at least one of nucleotide moieties $Y_1$ through $Y_n$, $R^1$ is $BR^5$ and $R^5$ is T (an apoluminescer); or, alternatively, $R^2$, $R^3$, or $R^4$ comprises a moiety T.

Adjacent nucleotides are covalently linked by formation of 3'-5' phosphodiester bonds. Superscript n, indicating the number of nucleotides, modified or unmodified, is an integer which can vary between 2 and 500. Preferably, n will have a value between 5 and 50. In general, probes comprising synthetic oligonucleotides will consist of relatively few total nucleotides, while probes derived from nucleic acid digest products will have a greater number of total nucleotides.

Base residue B can be any purine, modified purine, pyrimidine, or modified pyrimidine base capable of stable incorporation into a single-stranded polynucleotide without significantly affecting the capacity of the polynucleotide to form hybrids with target polynucleotides having substantial complementarity. However, a common feature of all base residues B useful in the present invention is a point or points suitable for attachment, preferably covalent, of a catalyst or an apoluminscer as the case may be. Thus, apart from the "classic" bases adenine, guanine, cytosine, uracil and thymine, other, less common bases, e.g., 5-methylcytosine, 5-hydroxymethylcytosine, orotic acid derivatives, methylated bases, e.g., 1-methylguanine, etc., can optionally be incorporated into the probes of the present invention.

Further, nucleotides Z and Z' can optionally comprise various substituents, which can be linked to either base or sugar portions, and which do not deleteriously affect the capability of the resulting polynucleotide to form hybrids with complementary target polynucleotides.

Polymer "tails" comprising a number of nucleotides appropriate for conjugation to catalyst or apoluminescer can be added to probe polynucleotides by use of calf-thymus terminal deoxynucleotidyl transferase (TdT), which catalyzes the addition of deoxynucleotides to the 3'-hydroxyl ends of single- or double-stranded DNA, as disclosed by Roychoudhury et al., *Nucleic Acids Res.* 3:101 (1976).

The catalysts and apoluminescers of the present invention can be coupled via a 5' phosphate or 3' hydroxyl linkage to one or more nucleotide moieties of $(X_1—X_n)$ or $(Y_1—Y_n)$, or, in the alternative, directly or by an ester or other linking group to a 2', 3' or 5' carbon atom of one or more of such nucleotide moieties.

Alternatively, the catalysts and apoluminescers can be coupled to nucleotide moieties through crosslinker or linking groups. "Crosslinker" or "linking group" refers to a moiety derived from a bifunctional molecule R'—L—R", wherein R' and R" are the same or different and represent such functional groups as —NH$_2$, —CO$_2$H, —CO$_2$R, where R' and/or R" is for example, 2-hydroxypyridine, N-hydroxysuccinimide, —CO$_2$CH$_3$, other active esters, acylimidazole, maleimide, trifluoroacetate, diketene, imidoesters, sulfonate esters, imine, —CHO, 1,2-cyclohexanedione, glyoxal, sulfenyl halides, alpha halo ketones, azide, etc., and L is an alkylene or substituted alkylene group preferably of at least three carbon atoms. Alkylene chain L can be substituted with such common substituents as halogen, (I, Br, Cl, F), hydroxy, cyano, phenyl, amino, carboxy, alkyl, alkoxy and others. Further, the alkylene chain of linker L can be interrupted by one or more bivalent groups, e.g., —O—, —S—, —NH—, —CH=CH—, —C≡C—, phenyl, —SO$_2$—, etc. However, functional group R' must be capable of forming, under appropriate conditions, a covalent bond with a nitrogen or carbon atom of base residue B, a carbon atom on the sugar moiety (5'-c), or the OH of the 3'-c, and functional group R" must be capable of forming, under appropriate conditions, a covalent bond with a side chain or terminal amino, carboxyl, sulfhydryl, or carbohydrate group of the catalyst or apoluminescer. Thus, bifunctional molecule R'—L—R" is reacted by apropriate techniques with a base (or sugar) residue or modified base (or sugar) residue of a nucleotide forming a conjugate of base residue B (or sugar) and said nucleotide joined by an amide, ester, amine, imine, sulfonamide, thioester, phosphate, or thiophosphate linking group L, collectively forming moiety Z or Z' as the case may be. Clearly, the choice of linkinq group R'—L—R" and a particular conjugation chemistry must reflect the need to preserve other macromolecular bonds critical to the integrity of the resulting probe molecule, i.e., peptide, N-glycosidic, and phosphodiester bonds.

Examples of bifunctional molecules include N-succinimidyl 4-glyoxalylbenzoate, carbonyl imidazole, dimethyl suberimidate, 1-ethyl,3-dimethylaminopropyl-carbodiimide (EDAC), para-nitrophenyl 3-(2-bromo, 3-ketobutylsulfonyl)propionate or other active esters, glutaraldehyde, substituted alkenes of the general formula NH$_2$(CH$_2$)$_n$NH$_2$, and other suitable equivalents.

After hybridization, a substrate for the catalyst is added. The catalyst then acts upon the substrate and converts it to a transformation radical. It is important to remember that the substantially mutually exclusive regions of the target analyte to which the labeled probes have hybridized must be sufficiently close enough to permit the hydroxy radical generated by the catalyst's action on an appropriate substrate, to convert the apoluminescer to a luminescer.

After hybridization has taken place, the sample must be exposed to a means for exciting the luminescer. This can generally be accomplished by irradiating the sample with the appropriate light wavelength. By "appropriate" is meant a wavelength within the absorption spectrum of the luminescer. If the luminescer is present in the sample, it will absorb the light energy and re-emit such energy as light of a different wavelength. The detection of this light response can be accomplished with numerous detection devices which are commercially available e.g., a spectrofluorimeter. Such secondary emissions of light energy can only occur if hybridization has taken place. Hence, the presence of the target nucleotide analyte is indicated by such secondary emissions, and the amount of target nucleotide analyte in the sample is related to the amount of secondary light emitted.

The present invention provides diagnostic kits for detecting the presence of at least one target polynucleotide analyte in a physiological sample. By the term "kit" is meant a packaged combination of containers holding the necessary reagent elements for detecting the presence of at least one target analyte.

Where more than one target analyte is sought, the kit must comprise a multiple of catalyst-labeled probes within which there is one catalyst-labeled probe that is substantially complimentary to a first single-stranded region of each target analyte. The catalyst label employed may be the same or different for each target analyte. The kit must also comprise a multiple of apoluminescer-labeled probes within which there is one labeled probe that is substantially complimentary to a second single-stranded region of each target analyte, the second region being substantially mutually exclusive from the first region. The apoluminescer label used must be different for each target analyte. Finally, the kit must also comprise a substrate for the catalyst label(s), wherein the substrate is capable of conversion to a transformation radical by the catalyst(s).

The following Examples illustrate various aspects and embodiments of the subject invention. In the Examples, all parts and percentages are by weight unless otherwise indicated.

EXAMPLES

Preparation of DNA probes I and II

DNA probe I is prepared by synthetic oligonucleotide synthesis as commonly performed. It is a 50 base sequence corresponding to the M13 mP8 region designated from residue 976 to residue 1025. The sequence is: 5' . . . AGGTCGACGGATCCCGGGGAATTC-GTAA TCATGGTCATAGCTGTTTCCTG. . . 3'. This sequence is present in the M13 mP8 genome but is absent from the wild type phage.

DNA probe II is also prepared by standard synthetic oligonucleotide synthesis techniques. It is also a 50 base oligomer which corresponds to residues 1035 to 1084. The sequence is: 5' . . . GTTA TCCGCTCACAATT-CCACACAACATACGAGCCGGAG-CATAAAGTGTA . . . 3'. This sequence is also present in M13 mp8 DNA but is absent from the wild type phage. The intervening sequence from the 3'-terminal nucleotide of DNA PI to the 5'-terminal residue of DNA PII is 10 nucleotides although it could be as few as 1 or as many as 50. The 5'-phosphate form of these oligomers is prepared by standard synthetic or enzymatic procedures.

Preparation of rG tailed probe DNA

This procedure follows the method of Roychoudury. Jay and Wu (Nucleic Acids Research, 3:101–106 (1976)). 100 µg of DNA PI (or DNA PII) ($2.4 \times 10^{-8}$ moles 3'-ends/ml) and $1.3 \times 10^{-6}$ moles/ml of guanosine 5'-triphosphate (GTP) are incubated with $1 \times 10^{+5}$ units/ml of terminal deoxyribonucleotide transferase in a volume of 250 µl of 140 mM potassium cacodylate (pH 7.6) containing 30 mM tris-HCl, 0.1 mM dithiothreitol and 1 mM cobalt chloride for 4 hours at 37° C. The nucleic acid is isolated by filtration through a $1 \times 15$ cm Sephadex G-25 column eluted with distilled water. Analysis of the reaction by running a comparison reaction with [3H]-labeled GTP indicates the number of guanosine ribonucleotide residues added. This can be done in an analogous manner with DNA PII.

EXAMPLE I

HRP as Catalyst, Dadcafi as Apoluminscer, ($OH^-$) as Transformation Radical

Conjugation of Horseradish Peroxidase to Ribonucleotide Tailed Polydeoxyribonucleotides:

100 µg of DNA PI-rG (or DNA PII-rG) tailed DNA (606 nmoles 3'-ends/ml) is incubated in 0.1 mMole/ml sodium meta periodate ($NaIO_4$) for 30 minutes at 22° C. Horseradish peroxidase is added to a concentration of 60.6 nmoles/ml with the nucleic acid concentration now adjusted to 202 nmoles 3'-ends/ml and the mixture incubated for 2 hours at 25° C. Sodium borohydride ($NaBH_4$) is now added to a final concentration of 0.375 µmoles/ml, with a final nucleic acid concentration of 151 nmoles 3'-ends/ml, and the reaction is incubated for 3 hours at 4° C. The mixture is dialyzed against 10 mM $KPO_4$ (pH 7.4) containing 100 mM NaCl at 4° C. The resulting mixture is separated on a $0.7 \times 50$ cm column containing Sephadex G-100 by elution against the same buffer. Product DNA PI-HRP conjugate is identified in fractions absorbing at 260 nm, containing [3H] activity and peroxidase activity as confirmed by assay against diacetyl dichlorofluorescin.

Preparation of 2',7'-dichloro-5-aminofluorescin diacetate (DADCAFI) 3'-end conjugates:

Synthesis of the DADCAFI apofluorochrome procedes by the procedure of G. Steinbach (Acta Histochem. 49: 19–34, 1974). 100 g of 4-nitrophthalic acid and 100 g of 4-chlororesoricinol are mixed and melted at 180° C. for 4 hours. After cooling the mixture is finely ground and suspended in 200 ml of boiling 0.6 N HCl. The insoluble crude 2',7'-dichloro-5-nitrofluorescin is filtered in a Buchner funnel, washed with 5 l of boiling water and dried at 100° C. 100 g of the crude material is dissolved in 250 g of acetic anhydride and refluxed for 2 hours. Pure 2',7'-dichloro-5-nitrofluorescin crystallizes by cooling to 4° C. The compound is recovered by filtration in a buchner funnel and vacuum-drying at room temperature.

Reduction of 2',7'-dichloro-5-nitrofluorescin diacetate is performed as per the procedure of R. Brandt and A. Keston (Analytical Biochemistry 11: 6–9, 1965). Five grams (0.0094 moles) of 2',7'-dichloro-5-nitrofluorescin diacetate is dissolved in 195 ml of boiling ethanol to which 1.74 moles of glacial acetic acid is added. Five 2-gram portions of zinc dust is added and the mixture is stirred for 10 minutes. Another five grams of zinc dust is added and the mixture is stirred for 10 minutes more. The zinc is removed by filtration and the resulting 2',7'-dichloro-5-aminofluorescin diacetate (DADCAFI) recovered by precipitation from chloroform followed by vacuum filtration and drying. Verification of the compound structure is made by NMR, IR, and MS analysis.

100 μg (606 nmoles 3'-ends/ml) of DNA probe I-rG (or DNA PII-rG) is incubated in 0.1 mmole/ml of sodium meta periodate for 30 minutes at 22° C. Sodium bicarbonate-carbonate buffer (pH 9.5) is added to a concentration of 0.1 mmole/ml. DADCAFI is added to a concentration of 20.2 μmoles/ml (with the concentration of DNA now at 202 nmoles 3'-ends/ml). Sodium borohydride is added to a concentration of 375 μmole/ml, with a final DNA concentration of 151 nmoles 3'-ends/ml. The mixture is incubated at 4° C. for 3 hours. The resulting mixture is purified by filtration on Sephadex G-100 column chromatography, eluting with 10 mM $KPO_4$ (pH 7.4) containing 100 mM NaCl. Verification of the conjugation is made by 260 nm analysis, and assaying for fluorescence by first activating the apofluorochrome by treatment in 0.01 N NaOH, neutralizing and adding HRP and $H_2O_2$ and watching for the development of fluorescence emission at 520 nm.

Preparation of HRP 5'-P-DNA Probe:

100 μg of 5'-P-DNA PI (or II) ($2.4 \times 10^{-8}$ mole 3'-ends/ml) is incubated with $1 \times 10^{-4}$ mole/ml of EDAC in $1 \times 10^{-5}$ mole/ml morpholine sulfonic acid (MES), pH 5.0, for 1 hour. HRP is added to a final concentration of $3 \times 10^{-7}$ mole/ml in a final concentration of sodium bicarbonate-carbonate buffer (pH 9.5) of $1 \times 10^{-4}$ mole/ml, with a final DNA concentration of $3 \times 10^{-9}$ 3'-ends/ml. The mixture is allowed to incubate for 12 hours at 22° C. Purification is accomplished by chromatography on a 2×50 cm Sephadex G-100 column eluted with 10 mM $KPO_4$ (pH 7.4), containing 100 mM NaCl.

Preparation of DADCAFI 5'-P-DNA Probe:

100 μg of 5'-P-DNA PI (or II) ($2.4 \times 10^{-8}$ mole 3'-ends/ml) is incubated with $1 \times 10^{-4}$ mole/ml of EDAC in $1 \times 10^{-5}$ mole/ml MES buffer. (pH 5.0) for 1 hour. DADCAFI is added to a final concentration of $3 \times 10^{-7}$ mole/ml in a final concentration of sodium bicarbonate-carbonate buffer (pH 9.5) of $1 \times 10^{-4}$ mole/ml, with a final DNA concentration of $3 \times 10^{-9}$ mole 3'-ends/ml. The mixture is allowed to incubate for 12 hours at 22° C. Purification is accomplished by chromatography on a 2×50 cm Sephadex G-100 column eluted with 10 mM $KPO_4$, (pH 7.4), containing 100 mM NaCl.

Detection of M13 mp8 DNA:

Activation of DADCAFI conjugated Probe I or II DNA is accomplished by incubating the probe in 0.01 N NaOH for 30 minutes at 22° C. The pH is then neutralized by dilution into 10 mM $KPO_4$ (pH 7.0).

54 μg of DNA Probe I-rG-HRP and 54 μg of DNA probe-5'-P-DADCAFI are incubated with M13 mp8 DNA (0.1 μg to 1.0 pg) in 100 μl of 10 mM $KPO_4$ (pH 7.0) containing 100 mM NaCl at 22° C. for 1 hour. $H_2O_2$ is added to a concentration of $1 \times 10^{-7}$ M by adding 2 μl of $5.1 \times 10^{-6}$ M $H_2O_2$. The samples are vortexed and allowed to incubate for one hour at 22° C. Presence of M13 mp8 DNA is verified by exciting the samples in a microcuvette at 500 nm and observing the resulting 520 nm emission.

Similarly, a system could be utilized whereby DNA probe I is rG-DADCAFI and DNA Probe II is 5'P-HRP.

EXAMPLE II

HRP as Catalyst, Tyramine as Apoluminscer, (OH⁻) as Transformation Radical

Preparation of Tyramine conjugated to PROBE DNA:

100 μg (606 nmole 3'-ends/ml) of DNA probe I-rG (or DNA PII-rG) is incubated in 0.1 nmole/ml of sodium meta periodate for 30 minutes at 22° C. Sodium bicarbonate-carbonate buffer (pH 9.5) is added to a concentration of 0.1 mmole/ml. Tyramine is added to a concentration of 20.2 μmol/ml (with the concentration of DNA now at 202 nmol 3'-ends/ml). Sodium borohydride is added to a concentration of 375 μmoles/ml, with a final DNA concentration of 151 nmole 3'-ends/ml. The mixture is incubated at 4° C. for 3 hours and purified by Sephadex G-100 column chromatography, eluting with 10 mM $KPO_4$ (pH 7.4) containing 100 mM NaCl.

Preparation of Tyramine coupled to 5'-P-Probe DNA:

100 μg of 5'-P-DNA PI (or II) ($2.4 \times 10^{-8}$ moles 3'-ends/ml) is incubated with $1 \times 10^{-4}$ moles/ml of 1-ethyl-(3,3'-dimethylaminopropyl)carbodiimide (EDAC) in $1 \times 10^{-5}$ moles/ml MES buffer, pH 5.0 for 1 hour. Tyramine is added to a final concentration of $3 \times 10^{-7}$ moles/ml in a final concentration of sodium bicarbonate-carbonate buffer (pH 9.5) of $1 \times 10^{-4}$ moles/ml, with a final DNA concentration of $3 \times 10^{-9}$ moles 3'-ends/ml. The reaction is incubated for 12 hours at 22° C. Purification is accomplished by chromatography on a 2×50 cm Sephadex G-100 column eluted with 10 mM $KPO_4$ (pH 7.4) containing 100 mM NaCl.

Detection of M13 mp8 DNA:

54 μg of DNA probe I-rG-HRP and 54 μg of DNA probe I-5'-P-tyramine are incubated with M13 mp8 DNA (0.1 μg to 1.0 pg) in 100 μl of 10 mM $KPO_4$ (pH 7.0) containing 100 mM NaCl at 22° C. for one hour. $H_2O_2$ is added to a concentration of $1 \times 10^{-7}$ M by adding 2 μl of $5.1 \times 10^{-6}$ M $H_2O_2$ and tyramine is added to a concentration of $3.3 \times 10^{-6}$ M. The samples are vortexed and incubated for one hour at 22° C. The presence of M13 mp8 DNA is verified by exciting the samples in a microcuvette at 500 nm and monitoring the emission at 520 nm.

EXAMPLE III

HRP as Catalyst, Luminol as Apolyminscer, (OH⁻) as Transformation Radical

Preparation ot Luminol conjugated to Probe DNA-rG:

100 μg (606 nmol 3'-ends/ml) of DNA probe I-rG (or DNA PII-rG) is incubated in 0.1 nmole/ml of sodium meta periodate for 30 minutes at 22° C. Sodium bicarbonate-carbonate buffer (pH 9.5) is added to a concentration of 0.1 mmole/ml. Luminol is added to a concentration of 20.2 μmol/ml (with the concentration of DNA now at 202 nmole 3'-ends/ml). Sodium borohydride is added to a concentration of 375 μmole/ml, with a final DNA concentration of 151 nmole 3'-ends/ml. The mixture is incubated at 4° C. for 3 hours and purified by Sephadex G-100 column chromatography, eluting with 10 mM $KPO_4$ (pH 7.4) containing 100 mM NaCl.

Preparation of Luminol coupled to 5'-P-Probe DNA:

100 μg of 5'-P-DNA PI (or II) ($2.4 \times 10^{-8}$ mole 3'-ends/ml) is incubated with $1 \times 10^{-4}$ mole/ml of 1-ethyl- (3,3'-dimethylaminopropyl)carbodiimide (EDAC) in $1 \times 10^{-5}$ mole/ml MES buffer, pH 5.0 for 1 hour. Luminol is added to a final concentration of $3 \times 10^{-7}$ mole/ml in a final concentration of sodium bicarbonate-carbonate buffer (pH 9.5) of $1 \times 10^{-4}$ mole/ml, with a final DNA concentration of $3 \times 10^{-9}$ mole 3'-ends/ml. The reaction is incubated for 12 hours at 22° C. Purification is accomplished by chromatography on a $2 \times 50$ cm Sephadex G-100 column eluted with 10 mM $KPP_4$ (pH 7.4) containing 100 mM NaCl.

Detection of M13 mp8 DNA is carried out in the same manner as in the previous examples except that hybridization is detected by monitoring for light emitted at 430 nm.

EXAMPLE IV

Fe-EDTA as Catalyst, Dadcafi as Apoluminscer, ($OH^-$) as Transformation Radical Preparation of Fe-EDTA-DNA Probe:

Triethyl ethylenediaminetetraacetate is prepared by the procedure of R. W. Hay and K. B. Nolan (J. Chem. Soc., Dalton Trans. pp. 1348-1351 (1975)). The monoaminopropyl derivative is prepared by the procedure of R. Hertzberg and P. Dervan (Biochemistry 23:3934-3945, 1984). 100 mg of triethyl ethylenediaminetetraacetate (0.27 mmol) is combined with 48 mg (0.29 mmol) of carbonyldiimidazole in 2.5 ml of dry dimethylformamide at 22° C. for 30 minutes. 2.6 ml of 1,3-diaminopropane (31 mmol) is added and the solution allowed to stir at 22° C. for 24 hours. The product is purified and the triester blocking groups removed by standard procedures.

Preparation of 5'-P-Fe-EDTA:

100 µg of 5'-P-DNA probe ($2.4 \times 10^{-8}$ mole 3'ends/ml) is incubated with $1 \times 10^{-4}$ mol/ml of EDAC in $1 \times 10^{-5}$ mol/ml of morpholine sulfonic acid for 1 hour. 2.5 mg of EDTA-propylamine is added to give a concentration of $2.4 \times 10^{-6}$ mol/ml in a concentration of sodium bicarbonate-carbonate buffer (pH 9.5) of $1 \times 10^{-4}$ mol/ml with a final DNA concentration of $3 \times 10^{-9}$ mol 3'-ends/ml. The mixture is allowed to incubate for 12 hours at 22° C. Purification is accomplished by chromatography on a $2 \times 50$ cm G-100 column eluted with 10 mM $KPO_4$ (pH 7.4) containing 100 mM NaCl.

Detection of M13 mp8 DNA is carried out as above utilizing any appropriate probe combination, for example, DNA probe I-rG-EDTA-Fe : DNA probe II-5'P=DADCAFI; or DNA Probe I-rG=DADCAFI: DNA Probe II-EDTA-Fe.

What is claimed is:

1. A polynucleotide probe of the formula $(Y_1—Y_n)$ wherein $Y_1$ through $Y_n$ are the same or different nucleotide moieties which collectively form a polynucleotide sequence substantially complementary to a single-stranded region of a target polynucleotide analyte; provided that at least one of nucleotide moieties $Y_1$ through $Y_n$ comprises a nucleotide having an apoluminescer attached thereto.

2. The probe of claim 1 wherein the apoluminescer is a composition that when reacted with an ($OH^-$) radical is converted to a luminescer.

3. The probe of claim 2 wherein the apoluminescer is selected from the group consisting of activated diacetyldichlorofluorescin, homovanillic acid, p-hydroxyphenylacetic acid, tyrosine, luminol and p-hydroxyphenylpropionic acid.

4. A method for detecting the presence of a target polynucleotide analyte in a physiological sample, wherein the method comprises:

(a) contacting the sample, under hybridization conditions, with a first and a second polynucleotide probe, the first probe having a catalyst attached thereto and the second probe having an apoluminescer attached thereto, both probes being substantially complementary to substantially mutually exclusive single-stranded regions of the analyte, such that upon hybridization of both probes with the analyte, the catalyst and the apoluminescer are located close enough to each other to permit the catalyst to release from a substrate a transformation radical that subsequently transforms the apoluminescer to a luminescer;

(b) adding the substrate for the catalyst, the substrate being capable of conversion to a transformation radical by the catalyst, the radical being capable of converting the apoluminescer to a luminescer;

(c) irradiating the sample with incident light within the absorption spectrum of the luminescer; and (d) measuring the light emitted by the luminescer.

5. The method of claim 4 wherein the apoluminescer is a composition that when reacted with an ($OH^-$) radical is converted to a luminescer.

6. The method of claim 5 wherein the apoluminescer is selected from the group consisting of activated diacetyldichlorofluorescin, nomovanillic acid, p-hydroxyphenylacetic acid, tyrosine, luminol and p-hydroxyphenylpropionic acid.

7. The method of claim 4 wherein the catalyst is a composition capable of releasing an ($OH^-$) radical from the substrate.

8. The method of claim 7 wherein the catalyst is selected from the group consisting of horseradish peroxidase, hematin, EDTA-Fe III complexes and microperoxidase, and the substrate is selected from the group consisting of molecular oxygen, hydrogen peroxide, HCOOH, $H_3CCOH$, t-butylhydroperoxide, linoleic hydroperoxide, cholesterol 5-hydroperoxide and cumen hydroperoxide.

9. The method of claim 4 wherein the apoluminescer is a composition that when reacted with ($OH^-$) radical is converted to a luminescer and the catalyst is a composition capable of releasing an ($OH^-$) radical from the substrate.

10. The method of claim 8 wherein the apoluminescer is selected from the group consisting of activated diacetyldichlorofluorescin, homovanillic acid, p-hydroxyphenylacetic acid, tyrosine, luminol and p-hydroxyphenylpropionic acid.

11. A diagnostic kit for detecting the presence of a target polynucleotide analyte in a physiological sample, wherein the kit comprises:

(a) a first polynucleotide probe having a catalyst attached thereto and which is substantially complementary to a first single-stranded region of the analyte; and (b) a second polynucleotide probe having an apoluminescer attached thereto and which is substantially complementary to a second single-stranded region of the analyte; the second region being substantially mutually exclusive from the first region but close enough thereto such that upon hybridization of the first and second probes with the analyte, the catalyst and the apoluminescer are proximate enough to each other to permit the catalyst to act on a substrate to release a tansformation radical for conversion of the apoluminescer to a luminescer.

12. The kit of claim 11 further including a substrate for the catalyst, the substrate being capable of conversion to a transformation radical by the catalyst, the radical being capable of converting the apoluminescer to a luminescer.

13. The kit of claim 11 wherein the apoluminescer is a composition that when reacted with an ($OH^-$) radical is converted to a luminescer and the catalyst is a composition capable of releasing an ($OH^-$) radical from the substrate.

14. The kit of claim 13 wherein the apoluminescer is selected from the group consisting of activated diacetyldichlorofluorescin, homovanillic acid, p-hydroxyphenylacetic acid, tyrosine, luminol and p-hydroxyphenylpropionic acid and the catalyst is selected from the group consisting of horseradish peroxidase, hematin, EDTA-Fe III complexes and microperoxidase, and the substrate is selected from the group consisting of molecular oxygen, hydrogen peroxide, HCOOH, $H_3CCOOH$, t-butylhydroperoxide, linoleic hydroperoxide, chloesterol 5-hydroperoxide and cumen hydroperoxide.

15. The kit of claim 13 further including a substrate for the catalyst, the substrate being capable of conversion to a transformation radical by the catalyst, the radical being capable of converting the apoluminescer to a luminescer.

16. The kit of claim 15 wherein the apoluminescer is selected from the group consisting of activated diacetyldichlorofluorescin, homovanillic acid, p-hydroxyphenylacetic acid, tyrosine, luminol and p-hydroxyphenylpropionic acid and the catalyst is selected from the group consisting of horseradish peroxidase, hematin, EDTA-Fe III complexes and microperoxidase, and the substrate is selected from molecular oxygen, hydrogen peroxide, HCOOH, $H_3CCOOH$, t-butylhydroperoxide, linoleic hydroperoxide, cholesterol 5-hydroperoxide and cumen hydroperoxide.

* * * * *